United States Patent [19]
Stack et al.

[11] Patent Number: 6,165,196
[45] Date of Patent: *Dec. 26, 2000

[54] PERFUSION-OCCLUSION APPARATUS

[75] Inventors: Richard S. Stack, Chapel Hill, N.C.; Francis G. Duhaylongsod, Honolulu, Hi.; Harry R. Phillips, III, Durham, N.C.; Troy Chapman, Englewood, Colo.; Michael Hogendijk, Palo Alto, Calif.; Hugh L. Narciso, Jr., Mountain View, Calif.

[73] Assignees: Corvascular Surgical Systems, Inc., Palo Alto, Calif.; Duke University, Durham, N.C.

[*] Notice: This patent issued on a continued prosecution application filed under 37 CFR 1.53(d), and is subject to the twenty year patent term provisions of 35 U.S.C. 154(a)(2).

[21] Appl. No.: 09/161,067

[22] Filed: Sep. 25, 1998

Related U.S. Application Data

[60] Provisional application No. 60/060,123, Sep. 26, 1997.

[51] Int. Cl.[7] .................................................. A61M 29/00
[52] U.S. Cl. .......................................... 606/194; 604/101
[58] Field of Search .................................... 606/191, 194, 606/108, 198; 604/96, 101, 103

[56] References Cited

U.S. PATENT DOCUMENTS

| | | |
|---|---|---|
| 3,477,474 | 11/1969 | Mesler . |
| 3,720,235 | 3/1973 | Schrock . |
| 3,865,776 | 2/1975 | Gergen . |
| 4,140,154 | 2/1979 | Kanao . |
| 4,167,953 | 9/1979 | Carlstrom . |
| 4,172,473 | 10/1979 | Lefere et al. . |
| 4,196,755 | 4/1980 | Kutnyak et al. . |
| 4,211,233 | 7/1980 | Lin . |
| 4,230,119 | 10/1980 | Blum . |
| 4,248,214 | 2/1981 | Hannah et al. . |
| 4,404,971 | 9/1983 | LeVeen et al. . |
| 4,445,892 | 5/1984 | Hussein et al. . |
| 4,520,823 | 6/1985 | LeVeen et al. . |
| 4,573,966 | 3/1986 | Weikl et al. . |
| 4,581,017 | 4/1986 | Sahota . |
| 4,666,426 | 5/1987 | Aigner . |
| 4,705,502 | 11/1987 | Patel . |
| 4,752,286 | 6/1988 | Okada . |
| 4,759,388 | 7/1988 | Kiyama et al. . |
| 4,771,777 | 9/1988 | Horzewski et al. . |
| 4,796,629 | 1/1989 | Grayzel . |
| 4,817,613 | 4/1989 | Jaraczewski et al. . |
| 4,830,694 | 5/1989 | Kanao . |
| 4,847,324 | 7/1989 | Creasy . |
| 4,857,054 | 8/1989 | Helfer . |

(List continued on next page.)

FOREIGN PATENT DOCUMENTS

| | | |
|---|---|---|
| 0 400 802 | 12/1990 | European Pat. Off. . |
| 0 791 332 | 8/1997 | European Pat. Off. . |
| 2 614 201 | 10/1988 | France . |
| 92/21398 | 12/1992 | WIPO . |
| 93/15785 | 8/1993 | WIPO . |

OTHER PUBLICATIONS

Stanford Univ. "ME210 Coronary Artery bypass Surgery: Minimally Invasive Techniques" (1995) http://me210abc.stanford.edu/94–95/projects/Pfizer/Spring/1.html.

Primary Examiner—Michael Buiz
Assistant Examiner—Kevin Truong
Attorney, Agent, or Firm—Morrison & Foerster LLP

[57] ABSTRACT

A perfusion-occlusion catheter provides an occluded region in a vessel to facilitate, for example, an anastomosis in the region, while providing a path for perfusing fluid (blood) through the path for delivery in the vessel downstream from the occluded region. According to one aspect of the invention, at least a portion of the catheter that effects vessel occlusion comprises a shield that when exposed to suture needles or like piercing instruments deflects or resists perforation.

36 Claims, 14 Drawing Sheets

U.S. PATENT DOCUMENTS

| | | |
|---|---|---|
| 4,877,031 | 10/1989 | Conway et al. . |
| 4,892,539 | 1/1990 | Koch . |
| 4,944,745 | 7/1990 | Sogard et al. . |
| 4,987,182 | 1/1991 | Creasy . |
| 5,001,305 | 3/1991 | Bartholomew . |
| 5,046,503 | 9/1991 | Schneiderman . |
| 5,059,375 | 10/1991 | Lindsay . |
| 5,069,662 | 12/1991 | Bodden . |
| 5,072,759 | 12/1991 | Moore . |
| 5,092,844 | 3/1992 | Schwartz et al. . |
| 5,106,363 | 4/1992 | Nobuyoshi . |
| 5,152,277 | 10/1992 | Honda et al. . |
| 5,176,638 | 1/1993 | Don Michael . |
| 5,180,376 | 1/1993 | Fischell . |
| 5,201,706 | 4/1993 | Noguchi et al. . |
| 5,290,306 | 3/1994 | Trotta et al. . |
| 5,312,344 | 5/1994 | Grinfeld et al. . |
| 5,320,604 | 6/1994 | Walker et al. . |
| 5,364,357 | 11/1994 | Aase . |
| 5,372,603 | 12/1994 | Acker et al. . |
| 5,452,733 | 9/1995 | Sterman et al. . |
| 5,458,574 | 10/1995 | Machold et al. . |
| 5,460,608 | 10/1995 | Lodin et al. . |
| 5,478,309 | 12/1995 | Sweezer et al. . |
| 5,484,412 | 1/1996 | Pierpont . |
| 5,599,307 | 2/1997 | Bacher et al. . |
| 5,613,979 | 3/1997 | Trotta et al. . |
| 5,620,649 | 4/1997 | Trotta . |
| 5,674,198 | 10/1997 | Leone . |
| 5,695,504 | 12/1997 | Gilford, III et al. . |
| 5,833,644 | 11/1998 | Zadno-Azizi et al. .................. 604/101 |
| 5,846,246 | 12/1998 | Dirks et al. ............................ 604/101 |

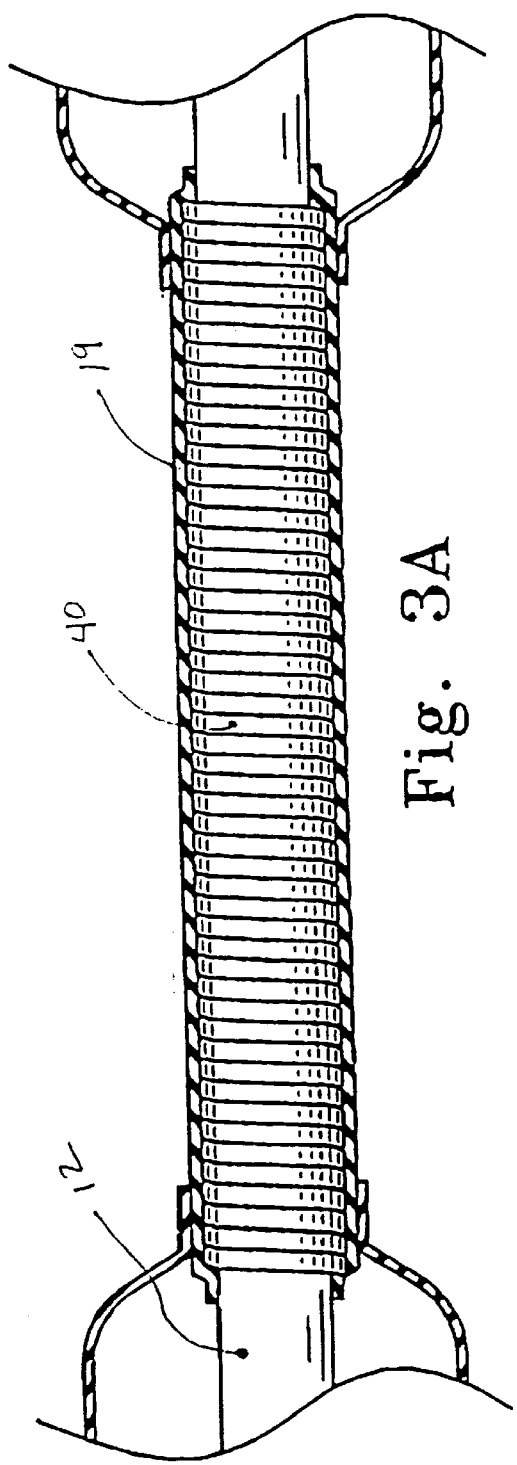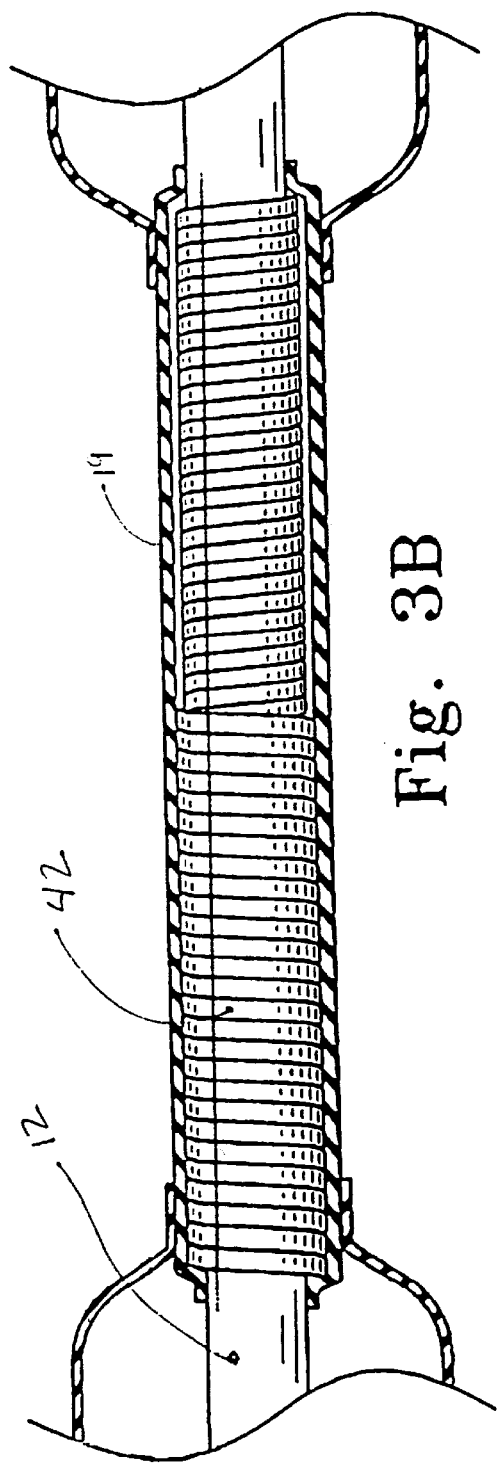

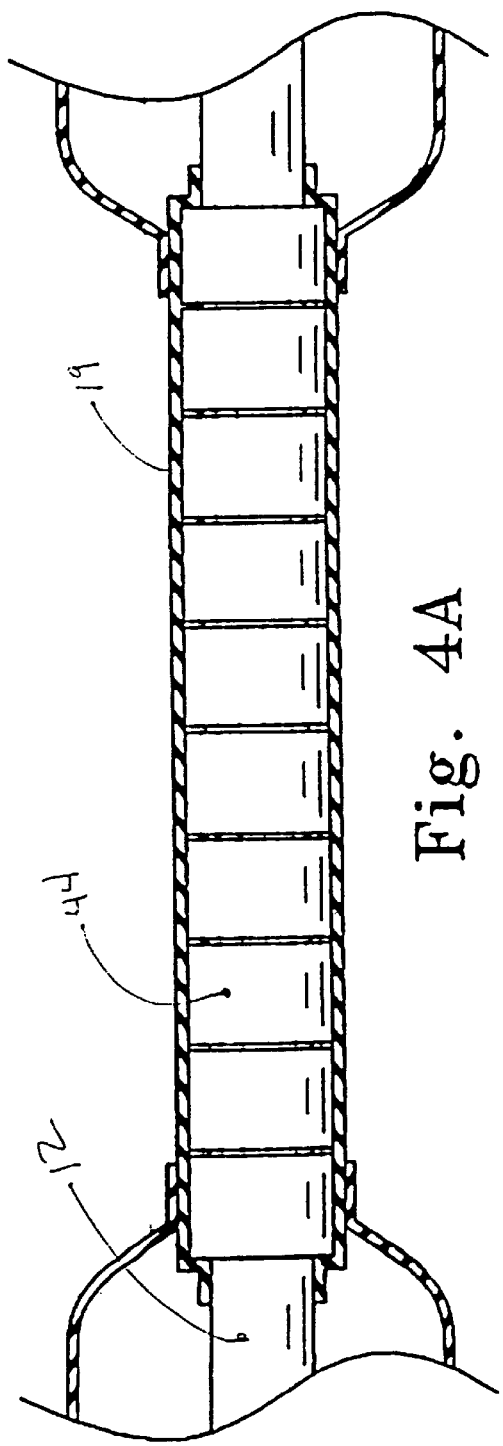
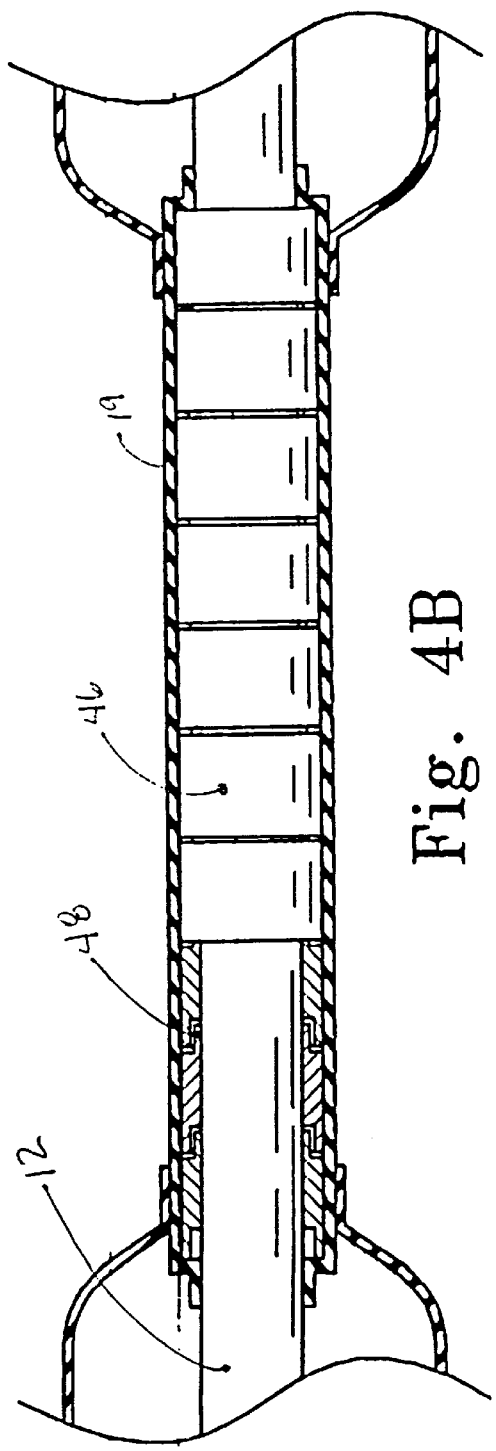

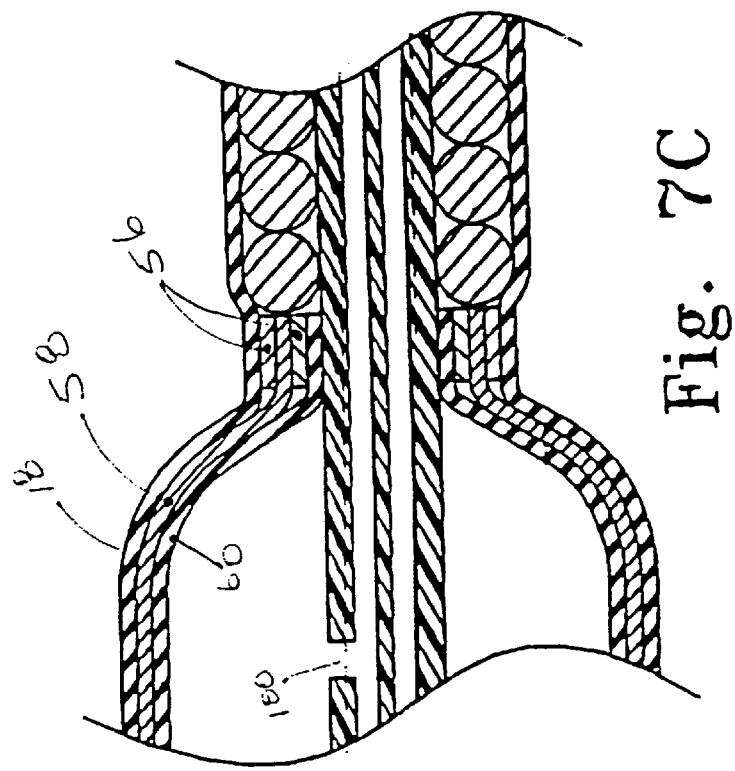
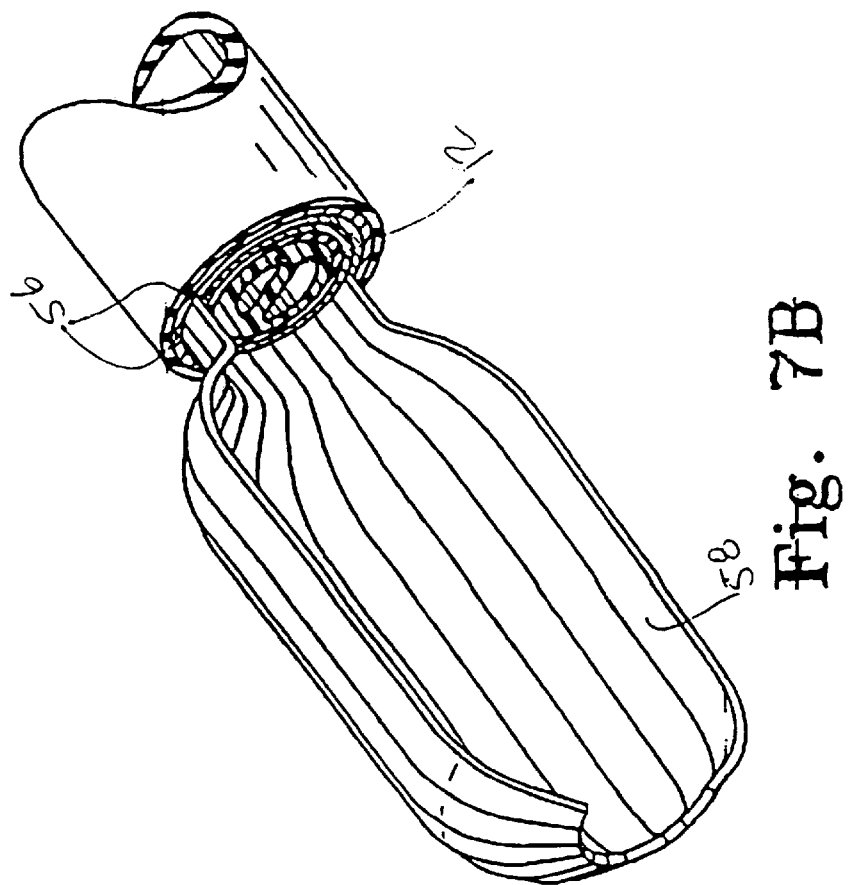

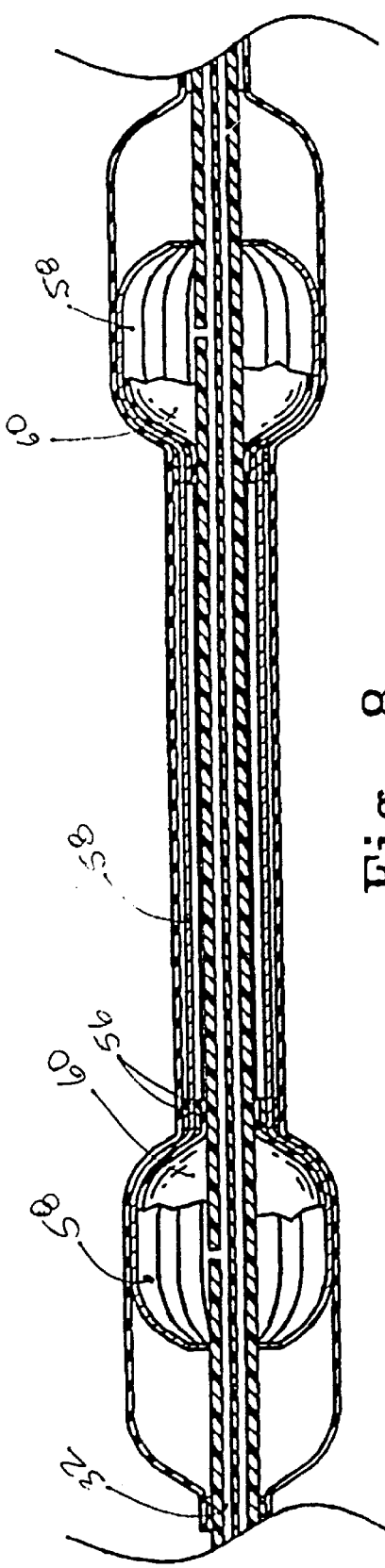
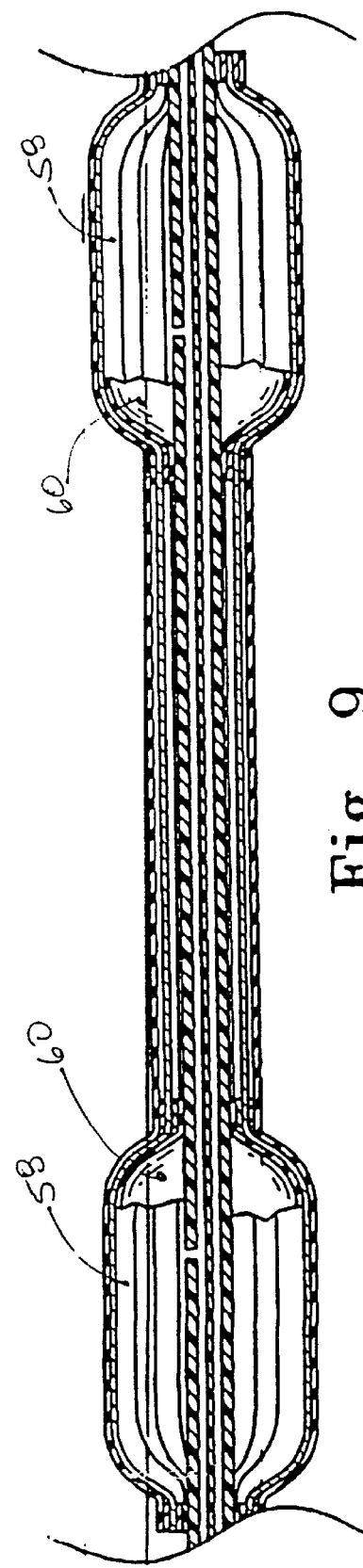
Fig. 8
Fig. 9

PERFUSION-OCCLUSION APPARATUS

CROSS REFERENCE TO RELATED APPLICATIONS

This application claims the benefit of U.S. Provisional Application Ser. No. 60/060,123, which was filed Sep. 26, 1997now pending, the disclosure of which is incorporated herein by reference.

FIELD OF THE INVENTION

The present invention relates to devices and methods for occluding a lumen(s) and perfusing fluid therethrough to, for example, facilitate the performance of coronary bypass procedures and other procedures on the heart and vessels.

BACKGROUND OF THE INVENTION

A manifestation of coronary artery disease is the build-up of plaque on the inner walls of the coronary arteries, which causes narrowing or complete closure of these arteries, resulting in insufficient blood flow to the heart. A variety of techniques have been developed for treating coronary artery disease. Where surgical intervention is necessary, stenoses of the coronary arteries can often be treated using endovascular techniques such as balloon angioplasty, atherectomy, stent placement and the like.

In cases where endovascular approaches are unsuitable or unsuccessful, coronary artery bypass graft procedures typically have been performed using open surgical techniques. Such procedures require an access technique known as median sternotomy, in which the patient's sternum is divided longitudinally and the chest spread to provide access to the heart. The patient's heart is arrested using cardioplegic agents and the patient is thereafter supported by a cardiopulmonary bypass system. A source of arterial blood is then connected to the coronary artery downstream from the target stenotic portion. The arterial blood source may be a venous or arterial graft vessel connected between an arterial source such as the aorta and the coronary artery. Another common arterial blood source is the left or right internal mammary artery which may be grafted to the coronary artery downstream of the stenosis or occlusion.

For a mammary arterial graft to be used in a coronary artery bypass procedure, blood flow through the target mammary artery must be temporarily stopped. Thus, in conventional open chest procedures, a clamp is applied, typically by hand or with forceps, directly to the mammary artery at a position downstream from the patient's aorta. After the mammary artery is clamped, it is ligated and divided at a location downstream from the clamp to create a free end which may be connected to the coronary artery. After completion of the grafting procedure, the clamp is removed by the surgeon by hand or with open forceps to permit blood flow through the mammary artery and into the coronary artery downstream of the blockage.

There are risks and difficulties associated with undergoing a procedure as described above. For instance, stopping the heart beat using cardioplegic agents and placing the patient on a cardiopulmonary bypass system is highly traumatic to the patient and often result in post-operative complications. As an alternative to the foregoing, there are approaches whereby the heart remains beating throughout the entire procedure. In addition, advances have been made in minimally invasive techniques to perform this procedure without opening the sternum, such as the thoracoscopic method described in U.S. Pat. No. 5,452,733 to Sterman, et al., the entirety of which is hereby incorporated by reference.

Another problem with conventional techniques is that blood flowing into the anastomosis site during the grafting portion of the procedure obstructs the surgeon's view of the critical suture placement of the anastomosis. Several devices and methods have been developed to limit or prevent blood loss through and into this anastomosis site. One method is to occlude the diseased target coronary artery with a suture, clamp or other occluding device both distal and proximal of the anastomosis site. The occlusion prevents blood flow into the anastomosis site both from retrograde and antegrade approaches. Dual balloon catheters, such as described in U.S. Pat. Nos. 4,520,823 and 4,404,971 to LeVeen, et al., are useful in obturating blood flow on both sides of a wound, or the site of a surgically detached aneurysm, while the wound is repaired.

Another approach is to direct a $CO_2$ jet at the anastomosis site during the procedure. This technique blows the blood out of the surgical site; however, it can result in injury to the targeted coronary artery, causing the endothelial layer of the vessel to be stripped away due to the force of the air jet.

Other improvements provide blood flow distal, or downstream, of the anastomosis site during the procedure. Occluding the anastomosis site by distal (single balloon) or distal and proximal (dual balloon) means without such perfusion can lead to myocardial ischemia and potential damage to the very heart muscle that the surgeon is trying to re-perfuse.

U.S. Pat. No. 4,230,119 to Blum discloses a microhemostat consisting of a bar that is inserted into a blood vessel by incision and whose ends are then inflated to occlude blood flow immediately adjacent the wound. The bar, however, forms a tube through which blood may flow during the procedure.

U.S. Pat. No. 5,106,363 to Nobuyoshi, the entirety of which is hereby incorporated by reference, discloses a conventional single balloon/dual lumen dilation catheter for use in dilating stenoses to improve blood through coronary arteries. This device utilizes a pump that delivers the patient's own blood from an intake in the catheter disposed in the patient's bloodstream proximal of the treatment site. The patient's blood is pumped through the outer sheath, then conducted to and through the inner lumen of the catheter, finally exiting into the patient's bloodstream. This device obviates the need for making an additional incision for blood intake, and also perfuses blood distal to the treatment site.

U.S. Pat. No. 4,581,017 to Sahota discloses a balloon perfusion dilation catheter which consists of holes located proximal and distal of the balloon so that when placed in a blood vessel, blood may flow to the vessel downstream of the occluded treatment site.

Likewise, U.S. Pat. No. 4,771,777 to Horzewski et al. describes a similar dual balloon perfusion catheter that can be used in conjunction with a pump to perfuse the patient's own blood to a region distal of the site being treated by the second dilatation balloon. The first balloon is used to form a blood seal between the catheter and a guiding catheter.

SUMMARY OF THE INVENTION

The invention involves improvements to devices and methods to facilitate performing coronary artery bypass and other procedures on the heart and vessels. According to one aspect of the invention, a perfusion-occlusion apparatus is provided for use in occluding a portion of a blood vessel and perfusing fluid through the blood vessel. The apparatus comprises a tube having at least one lumen, a proximal end and a distal end. First and second occlusion members are provided in the vicinity of the tube and spaced from one another to define an occlusion section. At least a portion of the occlusion section comprises a shield that when the shield is contacted by suture needles or like piercing instruments during a surgical procedure, it deflects the instrument or resists perforation. The invention may facilitate beating heart coronary bypass procedure, for example, by occluding the coronary artery distal and proximal to an anastomosis site and allowing for perfusion of tissue distal to the anastomosis site. The invention also eliminates or minimizes the risk of the surgeon's needle perforating the perfusion-occlusion device and possibly catching the back wall of the coronary artery being bypassed during the suturing of the graft. Further, the apparatus supports the vessel wall region between the occlusion members to facilitate a local surgical procedure such as an anastomosis. It also may facilitate shaping the opening at the anastomosis site.

According to another aspect of the invention, a perfusion-occlusion catheter is provided with a portion that may illuminate a region for identifying vessels (such as mammary artery) or regions of a vessel such as an anastomosis site. The illumination also may be used to prepare a mammary artery for use in an anastomosis (e.g., identify branches for removal).

According to another aspect of the invention, a system for use in occluding a portion of a vessel lumen and actively perfusing fluid through the vessel lumen is provided. The system comprises a catheter having a tube having at least one lumen and a proximal end and a distal end, and first and second occlusion members coupled to the tube and spaced from one another to provide an occlusion section; a catheter introducer sheath adapted to be inserted into a patient's vasculature; and a pump adapted to be fluidly coupled to the tube and the introducer sheath for pumping fluid from the introducer sheath to the distal end of the tube.

According to another aspect of the invention a system for use in occluding a portion of a vessel lumen and actively perfusing fluid through the vessel lumen is provided. The system comprises a catheter having a tube having first, second and third lumens, a proximal end and a distal end, and first and second occlusion members coupled to the first lumen and spaced from one another to provide an occlusion section the second lumen having at least one opening proximal to the occlusion section and the third lumen having at least one discharge opening distal to the occlusion section; and a pump fluidly coupled to the second and third lumens for driving fluid from said opening in said second lumen to the discharge opening in the third lumen.

According to yet another aspect of the invention, a perfusion-occlusion catheter is provided with a distal tip configuration to disperse fluid flow from the distal end of the catheter to minimize or eliminate the risk of fluid jetting from the catheter and possibly compromising vessel integrity downstream from the catheter.

According to another aspect of the invention, a method for identifying a vessel region prepared for an anastomosis is provided. The method comprises occluding a region of a vessel downstream from a blockage; and illuminating the region from a light source within the vessel.

The above is a brief description of some deficiencies in the prior art and advantages of the present invention. Other features, advantages, and embodiments of the invention will be apparent to those skilled in the art from the following description, accompanying drawings and appended claims.

BRIEF DESCRIPTION OF THE DRAWINGS

FIG. 3A is an elevational view of another shielded configuration according to the present invention.

FIG. 3B is an elevational view of another shielded configuration of the present invention.

FIG. 4A is an elevational view of another shielded configuration of the present invention.

FIG. 4B is an elevational view of another shielded configuration of the present invention.

FIG. 7B is a perspective view of the device of FIG. 7A, detailing the construction of the shielded occlusion section.

FIG. 7C is a cross-sectional view of the device of FIG. 7A, detailing the construction of the shielded occlusion section.

FIG. 8 is an elevational view of the distal region of the apparatus of the present invention having an occlusion section integrally shielded with overlapping leaves.

FIG. 9 is an elevational view of the distal region of the apparatus of the present invention having an occlusion section integrally shielded with overlapping leaves that extend through the length of the occlusion members.

DESCRIPTION OF THE INVENTION

Figure 1:
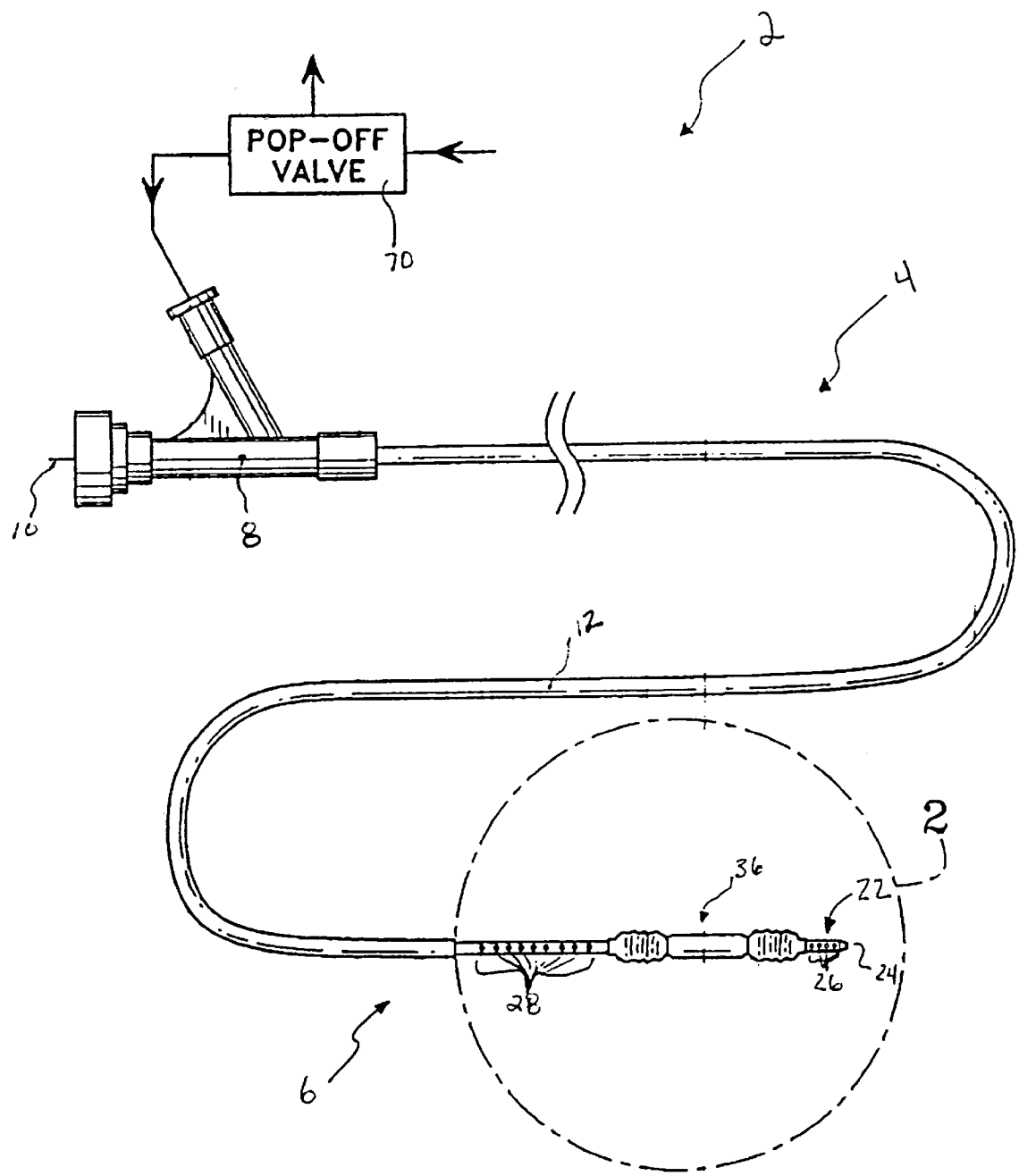
FIG. 1 is an elevational view of an apparatus constructed according to the present invention.

Referring to the drawings wherein like numerals indicate like elements, various embodiments of perfusion-occlusion methods and apparatus are shown in accordance with the principles of the present invention.

FIG. 1. depicts one embodiment of perfusion-occlusion apparatus according to the present invention and generally designated with reference numeral 2. Apparatus 2 is shown in a conventional catheter configuration with hub 8 at the proximal end of the apparatus. Perfusion-occlusion apparatus 2 has a proximal portion 4 and a distal portion 6. The catheter defines a tube 12 through which a conventional guidewire 10 passes.

Optionally attached to hub 8 is pop-off valve 70, which is in fluid communication with inflation lumen 32 (not shown) of tube 12. Pop-off valve 70 may be used as a safety device to ensure that any occlusion members such as balloons do not overinflate. Pop-off valve 70 is designed to activate to relieve the fluid pressure inside inflation lumen 32 if the pressure exceeds a predetermined limit which is chosen, with an appropriate factor of safety, to be below that of the inflation limit of the balloons. Preferably, this pop-off valve will be designed to activate at about 1.5 atmospheres of pressure.

Figure 2:
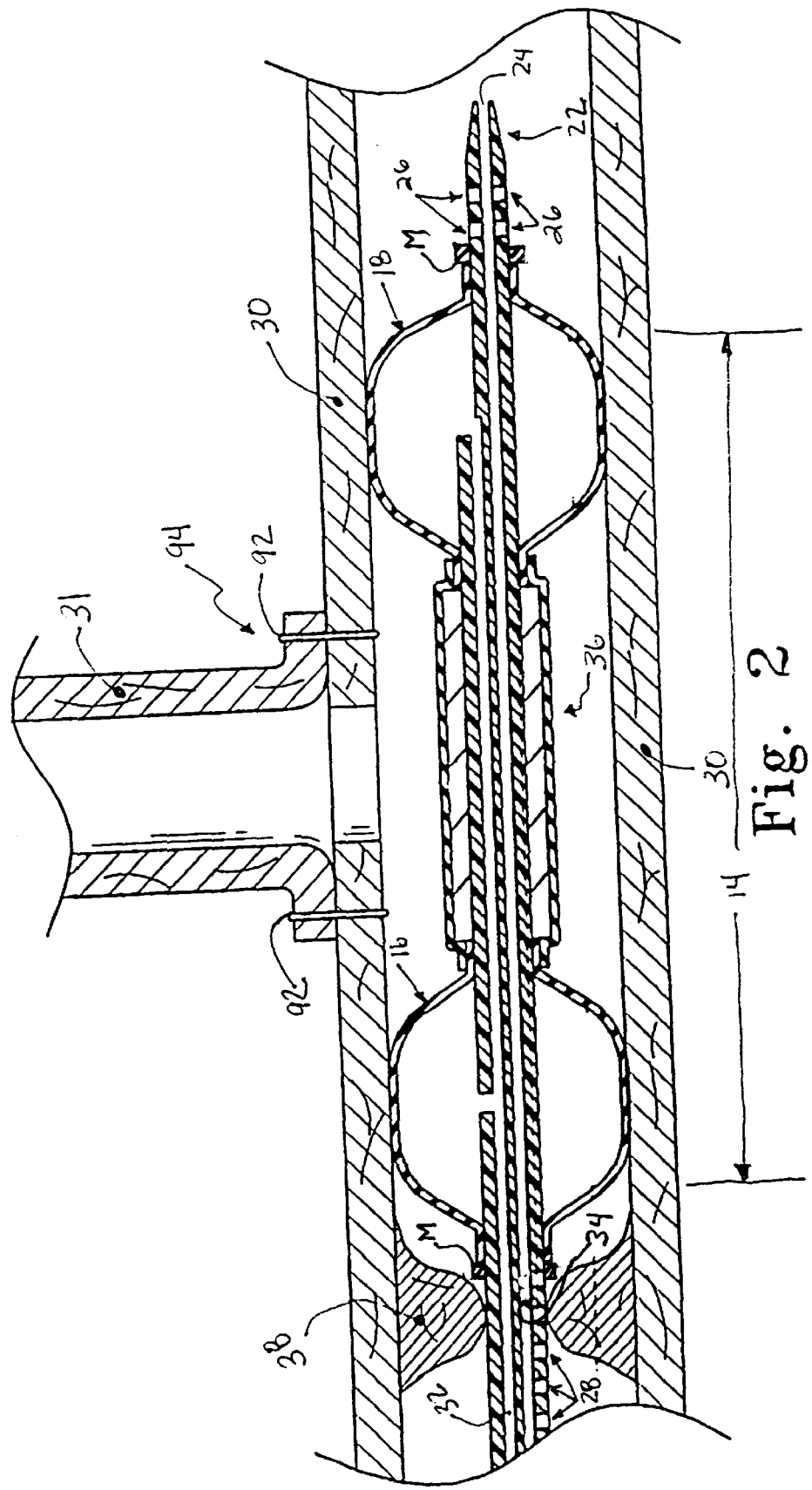
FIG. 2 is a cross-sectional view of the occlusion section of the apparatus shown in FIG. 1.

Disposed along tube 12 in the distal portion 6 of the perfusion-occlusion apparatus 2 is occlusion section 14, shown in greater detail in FIG. 2. At least a portion of occlusion section 14 comprises a shield that is resistant to perforation by a surgeon's suture needles or other like instruments.

Proximal of occlusion section 14 is a series of proximal apertures 28 in fluid communication with a lumen formed by tube 12 (FIG. 2) for the passive infusion of blood or any other suitable fluid into tube 12. Likewise, distal of occlusion section 14 is a series of distal apertures 26, which in the illustrative embodiment are in fluid communication with the same lumen (e.g., lumen 34) for the perfusion of blood or any other suitable fluid out of tube 12. Distal of distal apertures 26 is a distal tip 22 having distal tip opening 24 through which fluid and guidewire 10 may pass.

Referring to FIG. 2, occlusion section 14 as deployed in a diseased lumen 30, such as a cardiac artery, is shown. The lumen formed by vessel 30 contains a blockage or narrowing 38 proximal to occlusion section 14. Note that occlusion section 14 is disposed distal of blockage 38 and is centered beneath an anastomosis site 94, which is depicted here by the intersection of diseased vessel 30 and grafting vessel 31.

Longitudinally disposed within tube 12 is inflation lumen 32, which is fluidly connected to first occlusion member 16 and second occlusion member 18, and is used for the introduction of a fluid so to inflate occlusion members 16 and 18. When disposed distal (downstream, as blood flows, or right as shown in FIG. 2) of blockage 38, occlusion members 16 and 18 inflate to occlude diseased vessel 30 so that grafting vessel 31 may be joined at anastomosis site 94 by sutures 92 in a portion of vessel 30 relatively free from blood.

Preferably, and as depicted in FIG. 2, occlusion members 16 and 18 are conventional balloons made of any resilient biocompatible material such as polyethylene, PET, nylon, silicone and the like, as is well-known in the art, although occlusion members 16 and 18 may be any expanding member responsive to the introduction of a fluid, such as air, saline, blood, or any other appropriate fluid. Each of occlusion members 16 and 18 fluidly communicate with inflation lumen 32, yet remain separate members that may expand, contract, and otherwise operate independent of one another. However, and as depicted in FIG. 2, it is preferred that occlusion members 16 and 18 operate in tandem such that when a fluid is introduced through inflation lumen 32 into occlusion members 16 and 18, both members expand (and likewise contract upon the exiting of fluid) at substantially the same rate so to occupy approximately the same desired volume.

As shown in FIG. 2, occlusion members 16 and 18 are spaced along tube 12 and preferably define or form boundaries for an intermediate member or portion 36. Member 36 may be constructed to completely surround tube 12 of perfusion-occlusion apparatus 2. Member 36 also may be symmetrically disposed around tube 12. When deployed in diseased vessel 30, intermediate member 36 is placed below an anastomosis site 94 for the grafting of grafting vessel 31 onto diseased vessel 30 as will be further described below.

As noted, fluid lumen 34 is also longitudinally disposed within tube 12 as shown in FIG. 2. Fluid lumen 34 fluidly communicates with hub 8 on the proximal portion 4 of the perfusion-occlusion apparatus 2 and the distal tip 22 at the distal most end of perfusion-occlusion apparatus 2 to form distal tip opening 24. This fluid lumen 34 is for the passage therethrough of fluids such as blood, saline, or radiopaque dye, and is also configured for passage of guidewire 10 as is well-known in the art. Intermediate member 36 preferably is dimensioned to minimize the overall occlusion length (to prevent occluding the blood supply to collateral vessels in and around the occlusion section), while maximizing the anastomosis area in which the surgeon operates. In a preferred embodiment, the spacing between the outside edges of occlusion members 16 and 18 should be between about 10 to 20 mm, for example, about 15 mm. The diameter of occlusion members 16 and 18 will vary depending on the vessel anatomy into which the device is inserted, and will typically be between about 2 to 5 mm, for example, about 3 mm. Further, radiopaque markers (M) may be provided adjacent to the occlusion section as shown in FIG. 2, for example.

Proximal apertures 28 are located proximal of first occlusion member 16 along tube 12. Distal apertures 26 are disposed distal second occlusion member 18. Both proximal apertures 28 and distal apertures 26 are in fluid communication with fluid lumen 34. When deployed in a diseased vessel 30 and after occlusion members 16 and 18 are inflated to occlude vessel 30, arterial blood pressure forces blood through proximal apertures 28, through fluid lumen 34, and out distal apertures 26 and distal tip opening 24 into the bloodstream. In this way, blood is passively perfused downstream of the occlusion section 14 during the anastomosis procedure. It is preferred that proximal apertures 28 extend proximal of first occlusion member 16 a minimum distance of about 4 cm. This facilitates having perfusion apertures 28 extend upstream of the blockage being bypassed.

At least a portion of occlusion section 14 preferably is shielded so that when contacted by suture needles or like piercing instruments during a surgical procedure, it deflects such instruments or resists perforation. Referring to the embodiment illustrated in FIG. 2, such a shield is shown as being formed by intermediate member 36. Member 36, which may be tubular, is constructed to provide protection against perforation of the perfusion-occlusion apparatus 2 when sutures 92 are placed by the surgeon during the grafting procedure. It should be understood, however, that the shield may be provided in other forms. For example, occlusion members 16 and 18 the portion of tube 12 therebetween or member 36 or any combination or subcombination thereof may form the shield. This may be accomplished by way of the material properties or dimensions of the components of occlusion section 14, which are selected to form the shield so to provide the stiffness, strength, density, hardness, torsional and lateral deflection resistance, or any other property necessary to resist penetration or perforation by a surgeon's suture needle or like piercing instrument, which thus may differ from the remainder of apparatus 2 proximal and distal of occlusion section 14. For instance, the various members of occlusion section 14 may be made from various metals and their alloys, including stainless steel and radiopaque metals such as platinum, shape memory alloys such as nitinol, PVC, polycarbonate, HDPE, and other suitable biocompatible materials that will adequately serve to perform the above-mentioned duties. Alternatively the shield may be a discrete member provided with one or both of occlusion members 16 and 18 as will be described in more detail below.

Referring to FIG. 3A, intermediate member 36 is in the form of a coil 40. As shown in FIG. 3, coil 40 is made from a ribbon having a generally rectangular cross-section, although coil 40 may also be made of a wire having a substantially circular or elliptical cross-section and be within the scope of the invention. Coil 40 is disposed between occlusion members 16 and 18 so to substantially cover tube 12 therebetween and provide the desired protection. In the embodiment depicted in FIG. 3A, it is preferred that any gap (not shown) between coil windings be no greater than about 0.020 inch, and more preferably that there be no gap between coil windings. Coil 40 may be made of any material that adequately provides the desired protection, such as stainless steel, platinum, nitinol, HDPE, polycarbonate, and like materials. It is preferred that coil 40 be radiopaque so to provide a visual indication to the surgeon when viewed using standard fluoroscopic techniques.

A buffer or layer of material such as film 19 may be disposed around the exterior of coil 40 as shown in FIG. 3A, to for example, protect the structures (e.g., vessel wall) which interface with coil 40. Film 19 may additionally facilitate ease of movement of apparatus 2 through any guide catheter or the like. Although shown in FIG. 3A as a discrete layer bonded to tube 12 over coil 40 and under portions of occlusion members 16 and 18, film 19 can take on a number of configurations, including that of being extensions of occlusion members 16 and 18, as will be described in more detail below. It also should be understood that when disposed about tube 12, coil 40 allows for overall substantial flexibility of perfusion-occlusion apparatus 2 to enable apparatus 2 to navigate the tortuous vasculature or other bodily lumen paths to reach the desired site.

FIG. 3B depicts an alternative variation in which intermediate member 36 comprises an overlapping, counterwound coil 42 having the same general dimensions and properties as described for the coil 40 of FIG. 3A. Film 19 is also shown covering coil 40 as previously described. The aforementioned flexibility of apparatus 2 with counterwound coil 42 and the preferred radiopacity is present in this embodiment as well.

Turning now to FIG. 4A, intermediate member 36 is shown as a series of adjacent rings 44 fitted over tube 12 and disposed between occlusion members 16 and 18. Again, it is preferred that the gap between rings be no greater than about 0.020 inch, and more preferably that there be no gap between rings, to minimize or eliminate the possibility of a suture needle or like piercing instrument from reaching tube 12. Rings 44 may be made of any material that adequately provides the desired protection, such as stainless steel, platinum, nitinol, and like materials. It is preferred that rings 44 be radiopaque so to provide a visual indication to the surgeon when viewed using standard fluoroscopic techniques. The aforementioned flexibility of apparatus 2 with rings 44 and the preferred radiopacity is present in this embodiment as well.

FIG. 4B depicts a series of interlocking rings 46 which contain a reduced diameter section 48 over which fit the larger diameter portion of the immediately adjacent ring. This embodiment will ensure a tighter fit between interlocking rings 46, so that any gap between interlocking rings 46 is no greater than about 0.020 inch, or more preferably that there be no gap between interlocking rings 46, so that any suture needle or like piercing instrument cannot reach tube 12. Interlocking rings 46 may be made of any material that adequately provides the desired protection, such as stainless steel, platinum, nitinol, and like materials. It is preferred that interlocking rings 46 be radiopaque so to provide a visual indication to the surgeon when viewed using standard fluoroscopic techniques. The aforementioned flexibility of apparatus 2 with interlocking rings 46 and the preferred radiopacity may be present in this embodiment as well.

Figure 5:
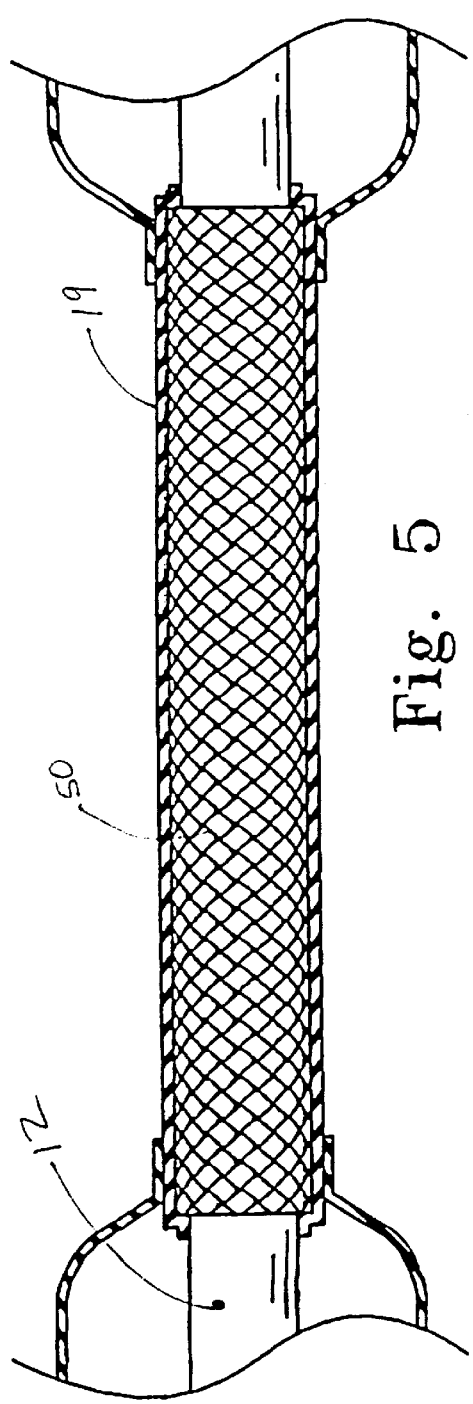
FIG. 5 is an elevational view of another shielded configuration of the present invention.

Yet another embodiment of the invention is shown in FIG. 5, where the intermediate section 36 comprise a braided ribbon 50. All of the preferred features regarding penetration resistance (e.g., filament spacing), radiopacity, and flexibility as previously described may be included for braided ribbon 50 as well.

Figure 6A:
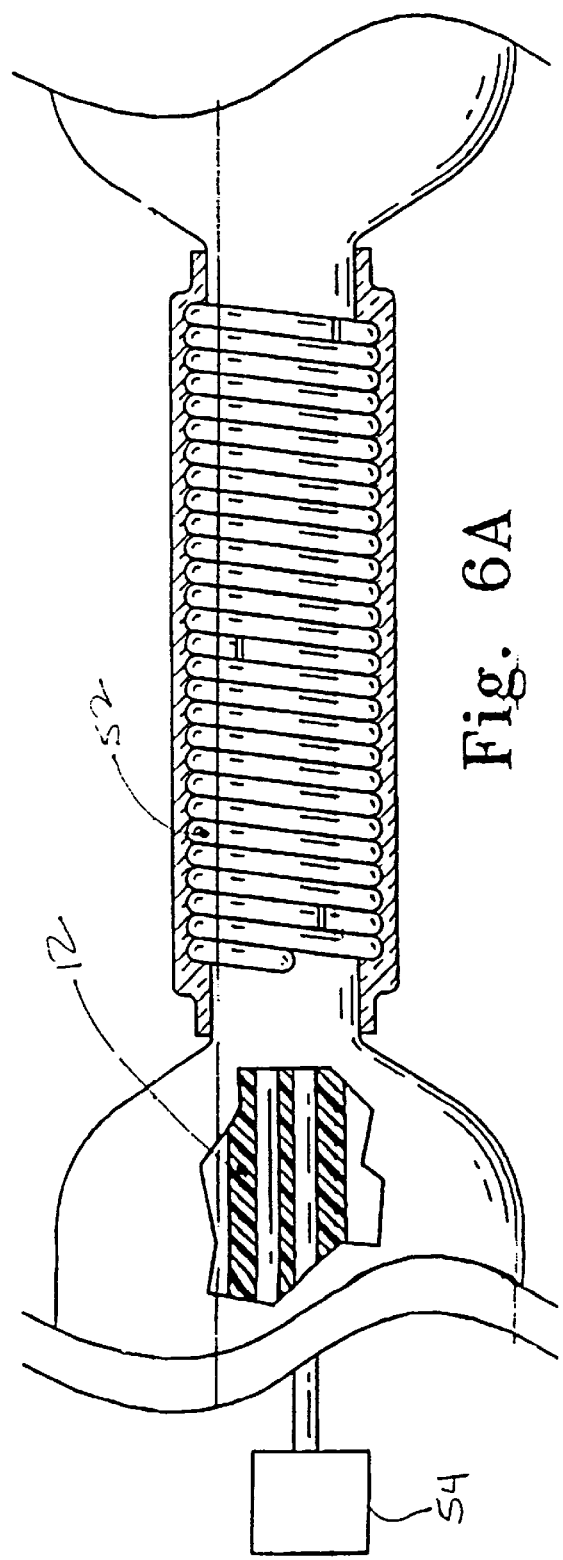
FIG. 6A is an elevational view of a shielded and illuminated configuration of the present invention.

FIG. 6A depicts an embodiment of the present invention wherein the shield comprises a fiber optic member 52 taking the form of a tightly wound coil. Although shown in FIG. 6A as a coil, fiber optic member 52 may take on any configuration effectively disposed about tube 12 so to provide the perforation resistance and/or flexibility as heretofore described as well as illumination of the anastomosis site, preferably adequate to aid the surgeon in performing the procedure. Fiber optic member 52 may be connected to light source 54 through tube 12 and illuminated by conventional means. Fiber optic member 52 may be configured, such as by making its outer surface rough, so that it provides circumferential illumination of substantially the entire anastomosis region. Alternatively, the coil may be sufficiently tightly wound to facilitate light emission from the coil (e.g., wound so that the fiber optic is bent beyond the critical angle).

Figure 6B:
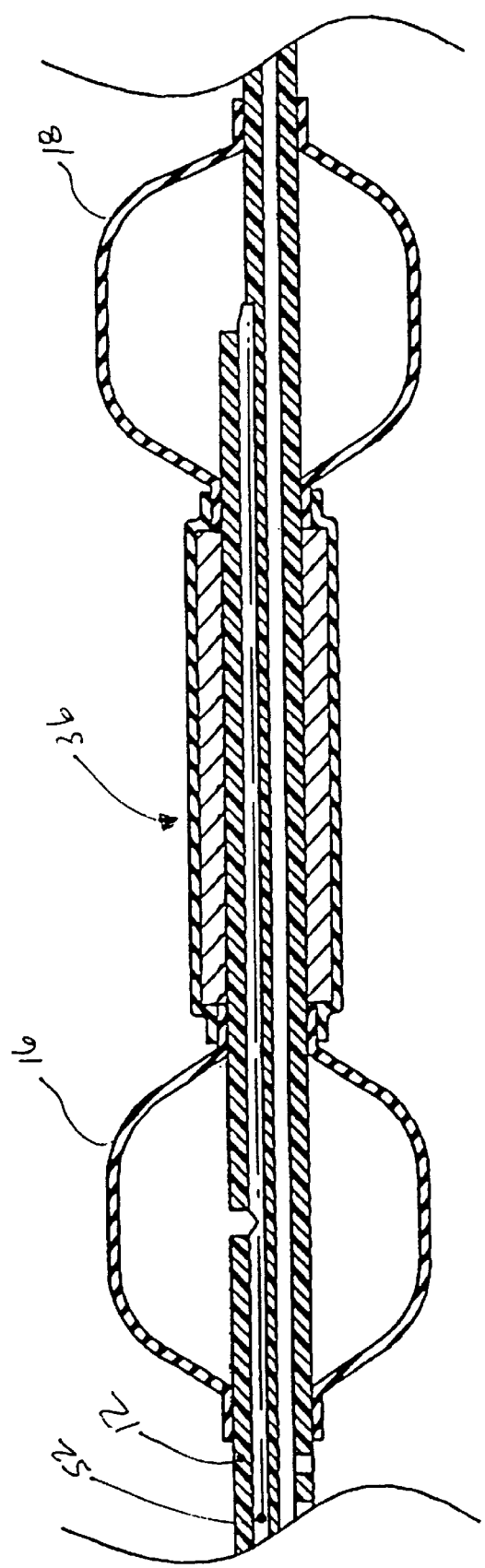
FIG. 6B is an elevational view of another shielded and illuminated configuration of the invention.

FIG. 6B shows an embodiment of the present invention wherein fiber optic member 52 is a single member disposed within tube 12 and configured so that first and second occlusion members 16 and 18 are substantially illuminated, such as by making its entire outer surface within the occlusion section 14 rough, or preferably selectively making portions of its outer surface rough so that only first and second occlusion members 16 and 18, alone or in combination, are illuminated.

According to another embodiment, first and second occlusion members 16 and 18 may be filled with an intralipid solution and the inflation lumen filled with saline or a solution of saline and contrast. One end of a fiber optic may be placed in the saline solution in inflation tube 32 and the other end of the fiber optic coupled to a light source, such as a laser or a broad-band light source. In the latter case, a wavelength of about 600 to about 700 mm is preferred since this range of wavelengths will facilitate the emitted light to pass through bodily tissue.

According to another embodiment of the invention, a protective shield, or sleeve, may be directly embedded into inflation lumen 32 or tube 12 in addition to or in lieu of the external protective shield provided about occlusion section 14. The shield or sleeve may be co-extruded with and extend along the entire length of the inflation lumen 32, or may extend along only a portion of its length in the vicinity of occlusion section 14, for example. The sleeve may comprise, for example, a solid, tubular thin-walled piece of metal, such as a shape memory alloy (i.e., nitinol), which is embedded into the wall thickness of the inflation lumen. The sleeve may be constructed and arranged to provide both flexibility and strength to the lumen to allow the distal portion of the device to deflect piercing instruments and to navigate through tortuous vessels. To enhance the flexibility of the protective nitinol sleeve, similar to a stent, one or more small rectangular openings may be provided in the sleeve by any suitable means, such as by laser etching, for example.

As described above, a portion or combination of portions of occlusion section 14 may be constructed to facilitate shielding. The occlusion section, for example, may be constructed such that (1) either one or both occlusion members may form shielding members as described above, (2) a substantial portion of one or both occlusion members in the proximity of the suturing section between the occlusion members forms shielding or (3) any combination of the above can be used alone or in combination with an intermediate shielded section as will be further apparent from the following description.

Figure 7A:
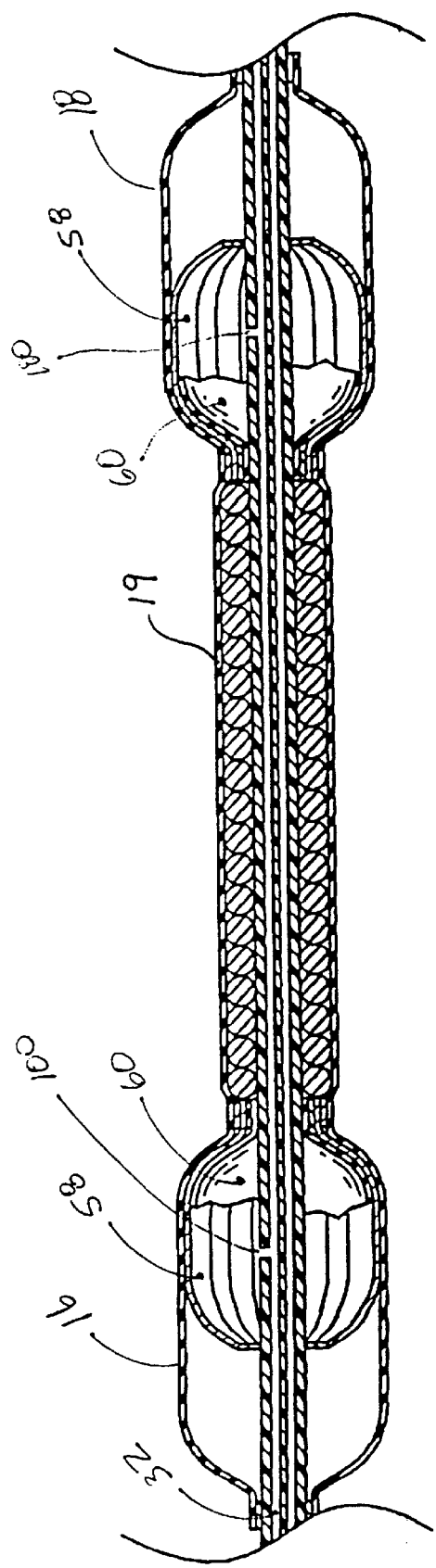
FIG. 7A is an elevational view of the occlusion section of the apparatus of the present invention having overlapping leaves shielding the first and second occlusion members and a separately shielded intermediate member.

Referring to FIGS. 7A, B & C, another shielding embodiment is shown. FIG. 7A shows an elevational view of an embodiment of the invention wherein both intermediate member 36 and occlusion members 16 and 18 are provided with shielding. A shield is shown in the form of substantially adjacent or overlapping leaves 58 that deploy as shown in FIG. 7B to occupy the interior of occlusion members 16 and 18. Overlapping leaves 58 may be made of a shape memory alloy, preferably nitinol, so that overlapping leaves 58 may deploy and retract properly.

Although not shown in the perspective of FIG. 7B for purposes of clarity, FIGS. 7A and 7C depict an expansion balloon 60 disposed between overlapping leaves 58 and tube 12. Expansion balloon 60 is fluidly coupled to inflation lumen 32 through port 100 so that when fluid enters expansion balloon 60, overlapping leaves 58 are deployed in occlusion members 16 and 18 to act as a shield.

FIG. 7C shows collar 56 disposed on the interior and exterior portions of overlapping leaves 58 adjacent intermediate member 36. Collar 56 serves to fix one end of the overlapping leaves 58 in place. A separate shield forming intermediate member 36 is shown in FIGS. 7A and 7C as a coil in this particular embodiment, advantages and features of which have been heretofore described.

Occlusion members 16 and 18 extend in the embodiment of FIG. 7A over intermediate member 36 and the coil to meet each other and form film 19. As previously described, film 19 may eliminate or minimize the risk of serve the coil of occlusion section 14 from abrading or damaging the interior of the tube, which may be a blood vessel, in which apparatus 2 is disposed. Film 19 may additionally facilitate ease of movement of apparatus 2 through any guide catheter or the like.

Referring now to FIGS. 8 and 9, variations of the embodiment shown in FIGS. 7A, B & C are shown. FIG. 8 depicts an integrally formed shielding variation of the overlapping leaves 58 previously described. In this embodiment, the nitinol arms comprising overlapping leaves 58 do not terminate at intermediate member 36 as in FIGS. 7A, 7B, and 7C, but rather extend continuously from first occlusion member 16 through intermediate member 36 to the second occlusion member 18. Collars 56 are still present to hold the nitinol arms of overlapping leaves 58 in place so that when expansion balloon 60 is filled with fluid, overlapping leaves 58 may expand to partially occupy occlusion members 16 and 18 as shown in FIG. 8. In this embodiment and those of FIGS. 7A, 7B, and 7C, the critical portion of occlusion members 16 and 18 for shielding is that portion immediately adjacent intermediate member 36. Accordingly, overlapping leaves 58 preferably selectively occupy these adjacent portions when deployed.

Referring to FIG. 9, another shielding configuration comprising overlapping leaves 58 is shown. In this version, the nitinol arms of overlapping leaves 58 extend when deployed to completely occupy occlusion members 16 and 18 to afford more extensive shielding. Overlapping leaves 58 extend all the way through occlusion members 16 and 18 in a direction away from intermediate member 36, and their ends, which are disposed about tube 12 in apparatus 2, are free-floating. This feature allows for the expansion and contraction of overlapping leaves 58 when fluid is introduced into expansion balloon 60.

Figure 10:
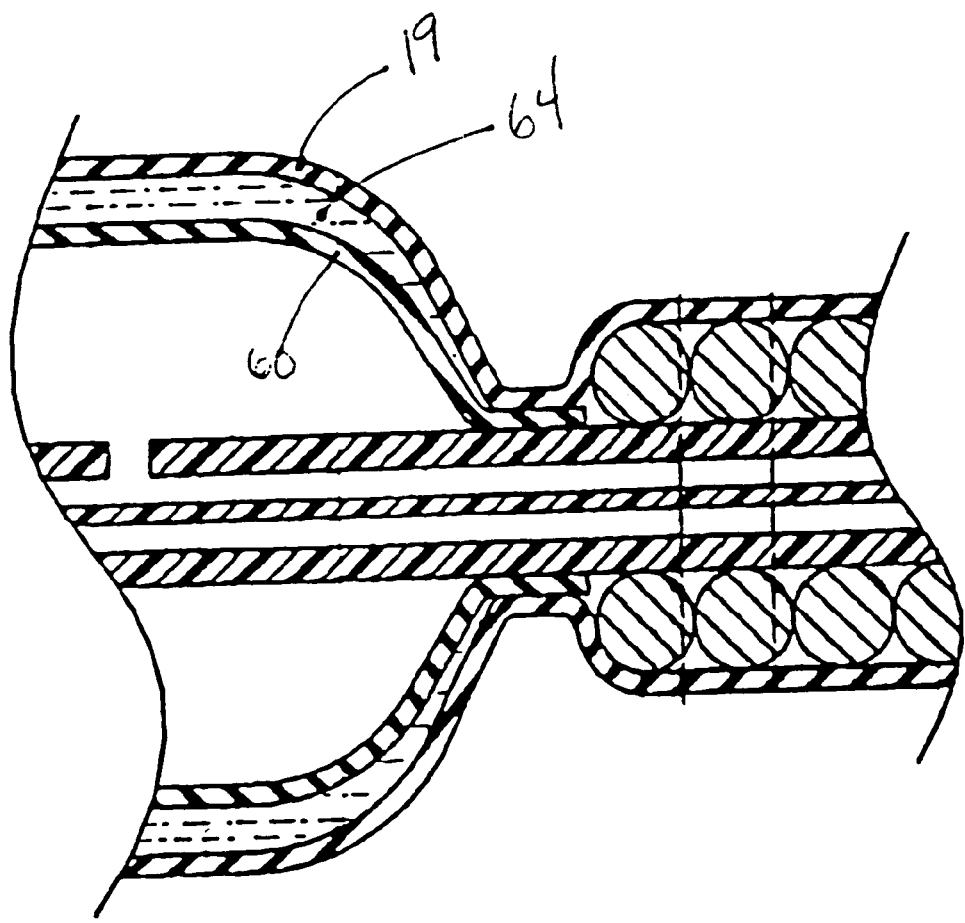
FIG. 10 is a detailed cross-sectional view of an occlusion member of the present invention having a fluid interposed between two expandable elements.

Referring to FIG. 10, another embodiment of the invention is shown. According to the illustrative embodiment, each occlusion member includes a buffer or layer, such as film 19, that extends over a portion of the intermediate member as described above, an expansion balloon 60 and a fluid 64 which, when the outer layer is punctured, flows into and seals the puncture. The fluid may be any biocompatible fluid having a viscosity with properties that will allow such punctures to be sealed in the temperature range of the human body.

Figure 11A:
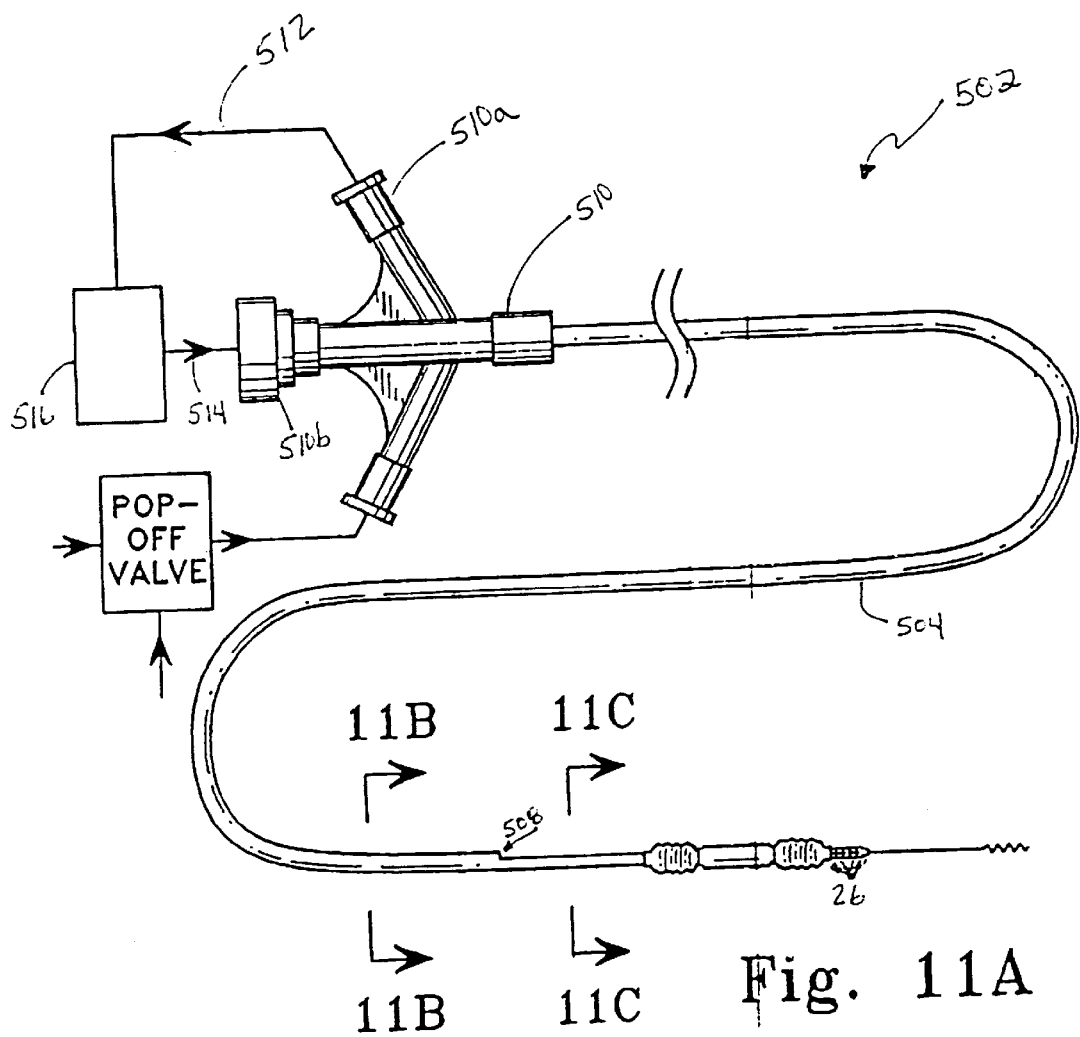
FIG. 11A is an elevational view of an active perfusion-occlusion apparatus of the present invention.
Figure 11B:
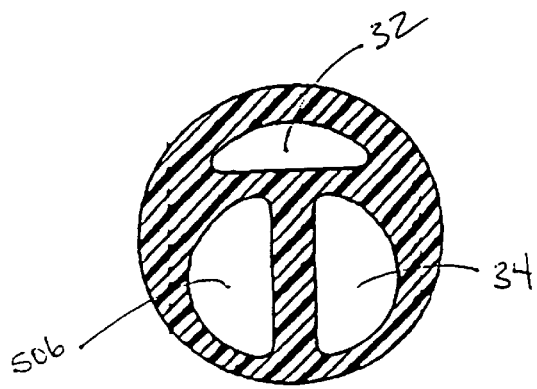
FIG. 11B is a cross-sectional view of the device of FIG. 11A detailing the fluid inlet, outlet, and inflation lumens.
Figure 11C:
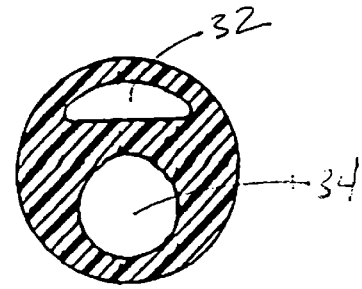
FIG. 11C is a cross-sectional view of the device of FIG. 11A detailing the fluid outlet and inflation lumens in the more distal region of the device.

According to another embodiment of the invention, a perfusion-occlusion catheter for active perfusion is provided. One active perfusion-occlusion apparatus constructed according to the present invention is shown in FIGS. 11A, 11B & 11C and generally designated with reference numeral 502. Apparatus 502 includes a perfusion occlusion catheter 504, which may have the same construction as the catheter shown in FIGS. 1 and 2 with the exception that proximal apertures 28 are not provided and additional lumen 506 for drawing fluid or blood from a lumen or vessel is provided. Lumen 506 has an opening to allow blood to be drawn (as indicated with arrow 508) from the region in a lumen or vessel in which the opening is positioned to a pump which then recirculates the blood through the catheter so that it may be discharged from the catheter's distal end. Catheter 504 further includes inflation lumen 32 and fluid transfer lumen 34. The former providing a conduit between inflatable occlusion members 16 and 18 and the latter providing a fluid path to distal apertures 26 downstream from the catheter occlusion section as described above.

Fluid withdrawal lumen 506 may be fluidly coupled to fluid transfer or delivery lumen 34 through a recirculation circuit as shown in FIG. 11A. Such a recirculation circuit may include hub arm 510a of three arm hub 510, conduits 512 and 514 (diagrammatically shown), pump 516 and center extension 510b of hub 510 all of which are fluidly coupled.

Figure 12B:
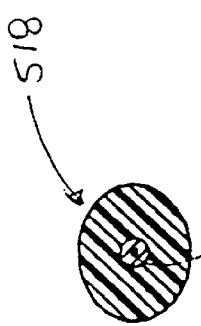
FIG. 12B is a distal view of the distal tip of the apparatus of the present invention illustrating passage of a guidewire through the distal tip.
Figure 12C:
FIG. 12C is a distal view of the distal tip of the apparatus of the present invention illustrating the distal tip in a relaxed condition with the guidewire removed.
Figure 12A:
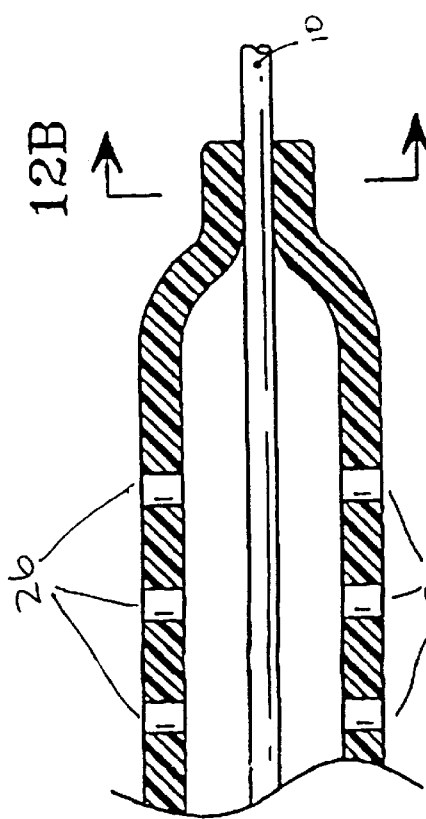
FIG. 12A is a cross-sectional view of the distal region of the apparatus of the present invention detailing a one-way valve for passage of a guidewire.
Figure 13:
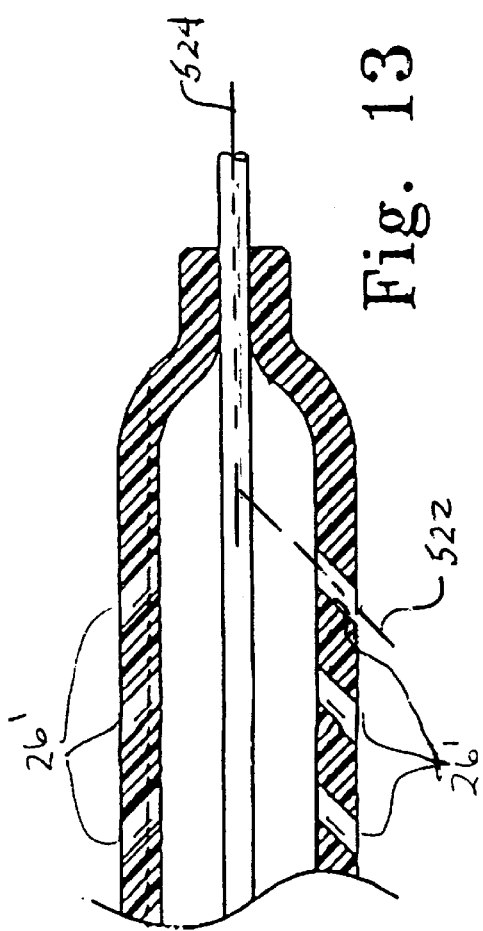
FIG. 13 is a cross-sectional view of another distal region configuration according to the present invention.

Referring to FIGS. 12A, 12B & 12C and 13, various embodiments of the distal end portion of catheter 504 are shown. As shown in FIGS. 12A, 12B and 12C, the distal end of catheter 504 may be provided with a one-way valve such as a duck bill valve generally designated with reference numeral 518. Valve 518 provides a seal around guidewire 10 (FIG. 12B) and minimizes or eliminates the possibility of fluid (e.g., blood) undesirably jetting out from catheter 504 due to pump pressures when, for example, guidewire 10 is removed (FIG. 12C). It is further noted that apertures 26 each preferably have a diameter less than or equal to 0.017 inch. This aperture size minimizes or eliminates the possibility of the guidewire undesirably passing through one of the apertures when guidewire 10 is pushed distally towards distal tip 22. The apertures also may minimize undesirable jetting at the distal end of the catheter. Alternatively, jetting may be minimized by removing distal apertures 26 and replacing them with a larger single discharge opening at the distal end of the device. In an alternative embodiment, the apertures may be configured as shown in FIG. 13 and designated with reference numeral 26'. Apertures 26' are formed in the catheter distal tip portion such that the center axis 522 of each aperture (or at least a plurality thereof) forms an angle with the longitudinal axis 524 of the lumen formed in the distal tip portion of the catheter that is less than or equal to 90 degrees, and more preferably is about 45 degrees.

Although a particular active perfusion configuration has been described, it is contemplated that other configurations may be used. The three lumen configuration can be replaced with a dual lumen configuration and the blood drawn through (1) the distal end of the guide catheter (i.e., the catheter used to deliver the perfusion-occlusion catheter), (2) a needle inserted into the patient's vasculature or (3) a catheter introducer sheath having provided in the wall thereof a plurality of perforations. As described above, the drawn blood can then be recirculated to the distal end of the catheter through the use of a pump. Alternatively, a blood transfusion bag may be used to deliver blood to the pump, which then pumps the blood through the catheter for delivery beyond the occlusion site.

Two exemplary procedures according to the present invention for occluding and perfusing a diseased coronary artery and grafting a healthy vein thereon are now presented. The methods herein described are illustrative only and in no way limit the variety of procedures in which the apparatus of the present invention can be used. For example, the apparatus may be used in a number of other surgical cardiac and vascular procedures, including mitral valve repair, mitral valve replacement, thrombectomy of the pulmonary artery, left atrium, or left ventricle, removal of atrial myxoma, atrial or ventricula septal defect closure, patent foramen ovale closure, tricuspid valve annuloplasty, tricuspid valve replacement, ventricular aneurysmectomy, thermal and mechanical cardia ablation procedures to correct arrhythmias, and the like. For these and other cardiac procedures, the apparatus of the present invention may be used during conventional open surgical techniques as described below, but may also be used in conjunction with minimally invasive endovascular techniques, such as that described in U.S. Pat. No. 5,452,733.

Additionally, the apparatus of the present invention may be used in other, non-cardiac procedures where the benefits of occluding and perfusing blood or other fluids through a lumen can be realized.

Figure 14A:
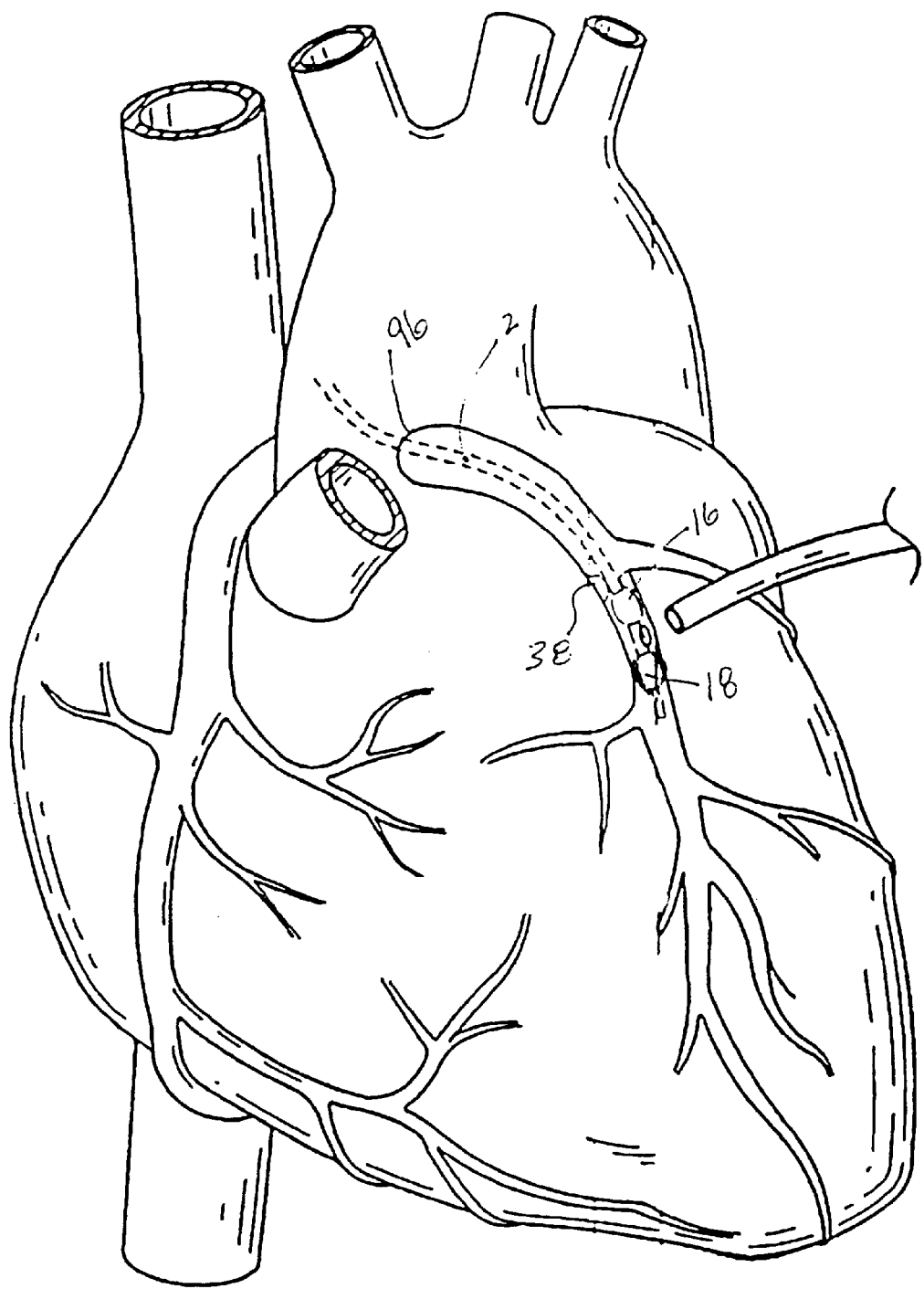
FIG. 14A illustrates the use of perfusion-occlusion apparatus of the present invention to occlude a section of a coronary artery distal to a blockage, while perfusing blood therethrough prior to suturing the internal mammary artery to the coronary artery, completing a coronary bypass graft.

Referring now to FIG. 14A, an exemplary use of the apparatus of the present invention in an open surgical coronary artery bypass graft procedure to create an anastomosis is presented. In this example, the left anterior descending coronary artery (LAD) contains a blockage or narrowing 38 as shown in FIG. 14A. If left untreated, this diseased artery may lead to insufficient blood flow and eventual angina, ischemia, and even myocardial infarction.

Figure 14B:
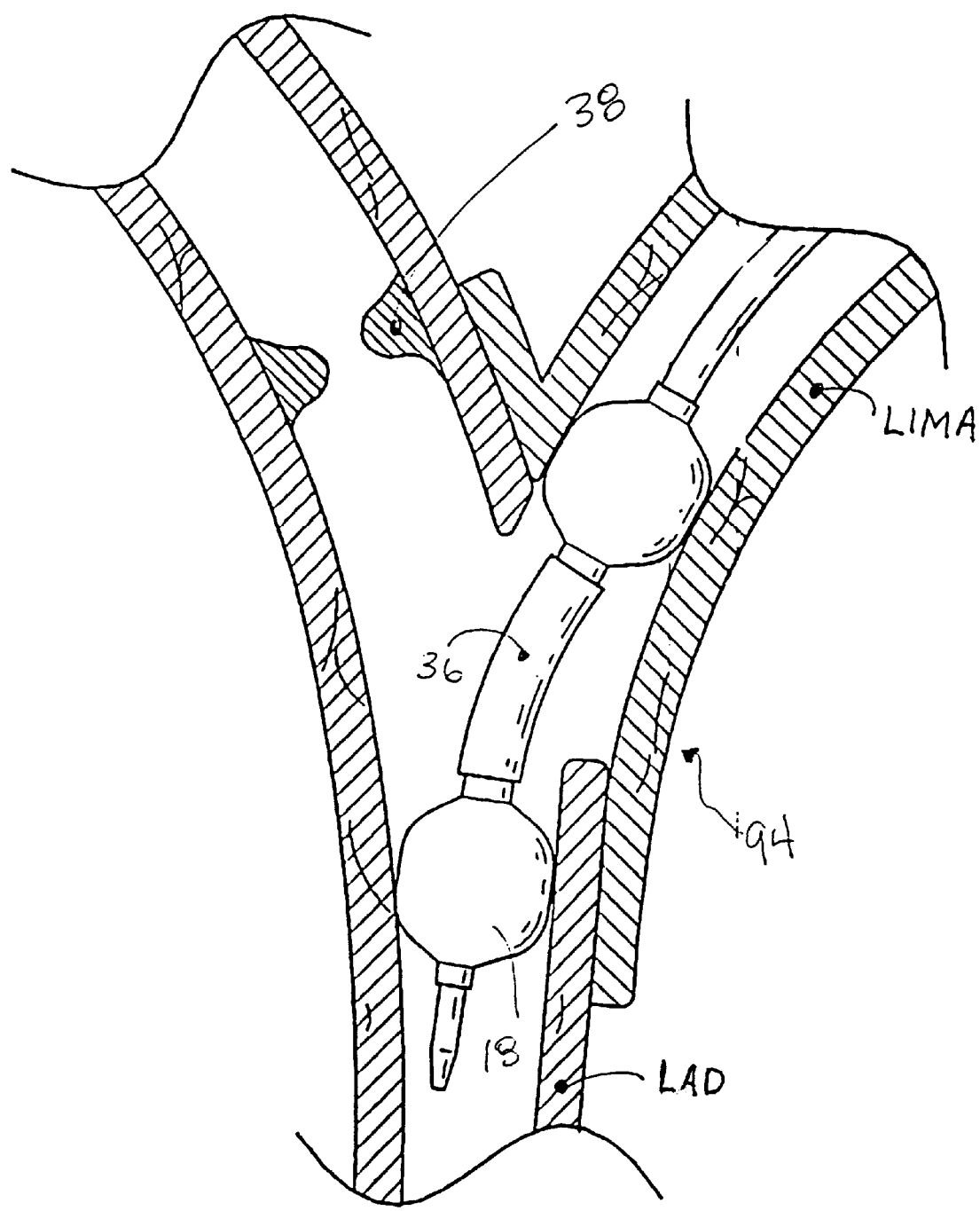
FIG. 14B illustrates perfusion-occlusion apparatus of the present invention partially extending through a section of the internal mammary artery and into a section of a coronary artery distal to a blockage so to occlude a desired portion of both arteries while perfusing blood therethrough prior to suturing the internal mammary artery to the coronary artery, completing a coronary bypass graft.

Conventional coronary bypass graft procedures require that a source of arterial blood be prepared for subsequent bypass connection to the diseased artery. Preferably, this source can be one of any number of existing arteries that are dissected in preparation for the bypass graft procedure. In many instances, it is preferred to use either the left or right internal mammary artery. Other appropriate sources include the gastroepiploic artery in the abdomen, the internal thoracic artery, and free grafts from the aorta using veins or arteries harvested from other locations in the patient's body as well as even synthetic graft materials. The upstream free end of the dissected artery, which is the arterial blood source, will be secured to the coronary artery at a location distal to the narrowing, thus providing the desired bypass blood flow. In the examples of FIGS. 14A and 14B, the left internal mammary artery (LIMA) will be used for this purpose.

Thus, according to the example of FIG. 14A, the patient undergoing the procedure is prepared according to known techniques for beating heart bypass procedures. To ready the patient for introduction of the perfusion-occlusion apparatus, both groins are prepared to permit access to the femoral arteries and veins. Alternatively, some procedures use the jugular vein as the access path for the apparatus 2. In addition, the abdomen will be prepared in case it is necessary to obtain access to an abdominal artery for use in the bypass procedure. The patient is placed under general anesthesia.

The LIMA is next dissected from the inner thoracic wall, and the side branches are sealed. The LIMA is then ligated using appropriate clips to temporarily occlude the artery before transsection, and further prepared for grafting according to conventional techniques.

Next, the left femoral artery (not shown) is accessed percutaneously or through an open cut in the groin with an introducer sheath. Other arteries suitable for accessing the ascending aorta may be used as well. A guide catheter (not shown) is inserted into the introducer sheath and directed through the patient's vasculature to locate the left coronary ostium, which marks the origin of the LAD.

Next, the perfusion-occlusion apparatus of the present invention, shown here as catheter 2, is inserted into the guide catheter behind a guidewire 10. The guidewire 10 should extend beyond the distal tip 22 of the perfusion-occlusion catheter 2 a preferable distance of 6 centimeters during navigation of the patient's vasculature.

Once the perfusion-occlusion apparatus 2 is placed in the left coronary ostium 96, guidewire 10 leads catheter 2 through the blockage or narrowing 38 of the LAD.

Conventional fluoroscopic techniques are next used to precisely position the occlusion section 14 of the perfusion-occlusion catheter 2 just downstream of the blockage or narrowing 38 in the LAD such that intermediate member 36 is centered in the artery at the location the anastomosis is to be performed. Alternatively, or in addition to the use of fluoroscopic techniques, any one of the illumination means herein described may be used to guide catheter 2 into the proper position.

At this point, first and second occlusion members, shown here as balloons 16 and 18, are inflated by introduction of a fluid through inflation tube 32. This occludes the LAD downstream of the blockage or narrowing 38, more particularly in that portion of the artery between the two balloons where the anastomosis is to be formed. Occluding the region onto which the LIMA will be grafted is of great advantage to the surgeon, whose view is not impeded by blood flowing in the area of interest.

Next, blood is perfused through the perfusion-occlusion catheter 2 from that portion of the LAD upstream of the blockage or narrowing to the rest of the artery downstream of the second balloon 18. Either the active or the passive perfusion-occlusion catheter 2, both of which are described above, may be used to perfuse the patient's blood. Note that for the active perfusion system previously described, blood may be preferably perfused from an effective source, such as a femoral artery, and not necessarily from a coronary artery or the like.

The role of the second occlusion balloon 18 distal and downstream of the first occlusion balloon may now be appreciated: this second balloon 18 isolates occlusion to an area where the anastomosis is to be formed while permitting blood to normally flow downstream of the second balloon in the LAD by means of the distal apertures 26, the distal tip 22 of the catheter 2, or both.

By using the perfusion-occlusion catheter 2 of the present invention, there is no need for the patient to undergo cardiopulmonary bypass during the procedure. Because the patient's blood is adequately flowing to all regions of the heart tissue except for that portion onto which the LIMA is to be grafted, this time-consuming and dangerous step of putting the patient on a cardiopulmonary bypass machine can be avoided.

After occlusion and perfusion of the anastomosis site is complete, the LIMA is then sutured onto the occluded portion of the LAD. As will be appreciated, the shielding present in all or selected portions of the occlusion section 14 of the perfusion-occlusion catheter 2 eliminates or minimizes the risk of provides protection to prevent the surgeon's suture needles, or like piercing instruments, from perforating the occlusion section 14 during the delicate and difficult grafting procedure. This added protection afforded by the shielding may greatly enhance the efficacy of the entire procedure. Additionally, as heretofore described, any one of a number of illumination means 52 may be used to illuminate all or a portion of the occlusion section 14 to aid the surgeon in positioning the perfusion-occlusion catheter 2 at the proper anastomosis site, and/or to visually indicate to the surgeon the location of the occlusion section 14 so that more precise suturing may be accomplished. Illumination means 52 may be particularly suited to those procedures performed endoscopically where light to assist the surgeon in performing the procedure is at a premium.

After the suturing is complete, the LIMA is joined to the LAD. The balloons 16 and 18 are deflated, and the entire perfusion-occlusion apparatus is withdrawn. Any temporary clips will next be removed from the LIMA to permit blood flow into the LAD.

Finally, the perfusion-occlusion catheter 2 will be removed, and all openings will be sutured using conventional techniques. The patient will then be recovered from anesthesia.

Next, an alternative method for performing anastomosis with the device of the present invention is presented in FIG. 14B. In this variation on the technique as above described, the occlusion section 14 of the perfusion-occlusion catheter 2 is positioned differently.

As shown in FIG. 14B, after the LIMA is prepared as described above, the perfusion-occlusion catheter 2 is placed in the LIMA through the subclavian artery until the distal end 22, including the distal occlusion member or balloon 18 and a portion of the intermediate member 36, extends out of the severed end of the LIMA. An incision is made in the LAD at the site of anastomosis 94, which is downstream of blockage 38. The region of the vessel in the vicinity (e.g., upstream) of the blockage may be closed with a clamp or suture prior to the forming the incision.

The distal tip 22 and balloon 18 is next placed inside the LAD and directed so that the distal tip 22 and balloon 18 extend downstream of the blockage or narrowing 38. The occlusion section 14 is precisely positioned so that the intermediate member 36 is centered about the anastomosis site 94.

Next, the left internal mammary artery LIMA is grafted onto the LAD at the selected anastomosis site by conventional suturing. The same shielding and illumination advantages may be applied during this variation of the method. This method has the advantages of more precise positioning of the occlusion section 14 of the perfusion-occlusion catheter 2 in the anastomosis site, and avoiding having to penetrate the blockage or narrowing 38 in the diseased artery. This lessens the risk that excess plaque, blood clot or like blockage material will dislodge from the artery wall during the procedure, potentially creating undesirable complications downstream in the heart. Other advantages not specifically described herein will be appreciated by those skilled in the art.

All references cited above are hereby incorporated herein by reference.

The above is a detailed description of a particular embodiment of the invention. It is recognized that departures from the disclosed embodiment may be made within the scope of the invention and that obvious modifications will occur to a person skilled in the art. The full scope of the invention is set out in the claims that follow and their equivalents. Accordingly, the claims and specification should not be construed to unduly narrow the full scope of protection to which the invention is entitled.

We claim:

1. A perfusion-occlusion apparatus for use in occluding a portion of a lumen and perfusing fluid through the lumen, comprising:

a tube having at least one lumen, a proximal end and a distal end; and first and second occlusion members provided in the vicinity of said distal end and spaced from one another to define an occlusion section having first, second and third portions, said first and second occlusion members being positioned in said first and third portions, at least a substantial portion of said occlusion section comprising an elongate shield that when contacted by suture needles or like piercing instruments along its length substantially resists perforation of said tube.

2. The apparatus of claim 1 wherein said second portion forms said shield.

3. The apparatus of claim 1 wherein said shield comprises an intermediate member coupled to said tube along said second portion and extending a substantial amount of the distance between said occlusion members.

4. The apparatus of claim 3 wherein said intermediate member comprises a coil.

5. The apparatus of claim 4 wherein said coil includes counterwound portions.

6. The apparatus of claim 3, further including a layer of material surrounding said intermediate member.

7. The apparatus of claim 3 wherein said intermediate member is radiopaque.

8. The apparatus of claim 1 wherein at least one of said first and second occlusion members comprise an inner and outer balloon and fluid disposed there between for sealing openings formed in said outer balloon.

9. The apparatus of claim 1 wherein said tube includes apertures formed therein proximal to said first occlusion member and distal to said second occlusion member.

10. The apparatus of claim 9 wherein said proximal apertures extend a minimum distance of about 4 cm from said first occlusion member.

11. The apparatus of claim 1 further including a pump adapted for coupling to said tube.

12. The apparatus of claim 1 wherein at least a portion of said tube includes three lumens.

13. The apparatus of claim 12 wherein two of said lumens are fluidly coupled to one another.

14. The apparatus of claim 13 further including a pump for driving fluid from one of said fluidly coupled lumens to the other.

15. The apparatus of claim 1 further including a one-way valve at one end of said tube.

16. The apparatus of claim 15 wherein said valve is a duck bill valve.

17. The apparatus of claim 1 wherein said tube includes a plurality of apertures formed distal to said second occlusion member, said tube and a plurality of said distal apertures each having a longitudinal axis, the angle formed between said longitudinal axis of said tube and the longitudinal axes of each of said plurality of distal apertures being less than or equal to ninety degrees.

18. The apparatus of claim 1 wherein said tube includes a plurality of apertures formed therein, proximal to said first occlusion member and extending from said first occlusion member a distance of about 4 to 7 cm in a direction away from said second portion.

19. The apparatus of claim 18 wherein said tube includes at least one opening distal to said second occlusion member and fluidly coupled to said apertures proximal to said first occlusion member, and an intermediate member being imperforate.

20. A surgical kit for preparing an anastomosis site comprising:

a catheter having a tube having at least one lumen and a proximal end and a distal end, at least first and second occlusion members coupled to said tube and spaced from one another to define an occlusion section in the vicinity of said distal end, and an elongate protective shield positioned about or within a substantial portion of said occlusion section to substantially resist perforation of said tube from a surgical cutting instrument or like piercing instrument; and instructions for use of said catheter for occluding a portion of a vessel lumen at the anastomosis site and perfusing fluid through the vessel lumen.

21. The apparatus of claim 1, further including an optic fiber optically coupled to at least one of said occlusion members for illuminating said occlusion member.

22. The apparatus of claim 1 wherein at least one of said first and second occlusion members forms said shield.

23. The apparatus of claim 22 wherein said shield comprises a plurality of overlapping elements at least disposed within one of said first and second occlusion members.

24. The apparatus of claim 23 wherein said overlapping elements are disposed in both of said first and second occlusion members.

25. The apparatus of claim 24 wherein said overlapping elements further surround said second portion.

26. The apparatus of claim 23 further including a balloon within at least one of said occlusion members, said overlapping elements extending around said balloon.

27. The apparatus of claim 26 wherein said overlapping elements form a substantially helical member when said balloon is expanded.

28. The apparatus of claim 26 wherein said overlapping elements form a substantially umbrella shaped member when said balloon is expanded.

29. The apparatus of claim 26 wherein said overlapping elements form a coil when said balloon is expanded.

30. The apparatus of claim 22 wherein at least one occlusion member includes an outer layer of material which surrounds said shield.

31. The apparatus of claim 3 wherein said intermediate member comprises a plurality of rings disposed about said tube.

32. The apparatus of claim 31 wherein a plurality of said rings interlock with other ones of said rings.

33. The apparatus of claim 3 wherein said intermediate member comprises a braided member disposed about said tube.

34. The apparatus of claim 3 wherein said intermediate member comprises an optic fiber wound around said tube.

35. The apparatus of claim 34 further including a light source, said light source being optically coupled to said fiber.

36. The apparatus of claim 34 wherein said optic fiber is arranged to illuminate said first and second occlusion members.

* * * * *